US009724507B2

(12) United States Patent
Wood et al.

(10) Patent No.: US 9,724,507 B2
(45) Date of Patent: Aug. 8, 2017

(54) INTERVENTIONAL MEDICAL SYSTEMS AND ASSOCIATED TETHERING ASSEMBLIES AND METHODS

(71) Applicant: Medtronic, Inc., Minneapolis, MN (US)

(72) Inventors: Rónán Wood, Galway (IE); Sean Ward, Dublin (IE); Paula McDonnell, Galway (IE); Pat McHugh, Ballyhaunis Co. (IE); Richard McEvoy, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 120 days.

(21) Appl. No.: 14/694,083

(22) Filed: Apr. 23, 2015

(65) Prior Publication Data
US 2016/0263372 A1   Sep. 15, 2016

Related U.S. Application Data

(60) Provisional application No. 62/132,662, filed on Mar. 13, 2015.

(51) Int. Cl.
*A61B 19/00* (2006.01)
*A61N 1/05* (2006.01)
(Continued)

(52) U.S. Cl.
CPC ........ *A61N 1/0587* (2013.01); *A61B 17/3468* (2013.01); *A61M 25/0105* (2013.01);
(Continued)

(58) Field of Classification Search
CPC ........ A61M 2210/125; A61M 25/0105; A61N 1/0587; A61N 1/372; A61N 1/37205;
(Continued)

(56) References Cited

U.S. PATENT DOCUMENTS 7,011,671 B2   3/2006   Welch
7,226,466 B2   6/2007   Opolski
(Continued)

OTHER PUBLICATIONS (PCT/US2016/020265) PCT Notification of Transmittal of the International Search Report and the Written Opinion of the International Searching Authority, mailed Sep. 22, 2016, 16 pages.
(Continued)

*Primary Examiner* — Katherine M Shi (57) ABSTRACT

An implantable medical device is tethered to a delivery catheter by a length of a tether, which extends through an attachment feature of the device and between a free end thereof and a secured end thereof, wherein the secured end is fixedly coupled to a tubular member of the catheter in proximity to a distal end thereof, and the free end is engaged against an inner surface of a sidewall that extends within the tubular member. The free end of the tether may be engaged against the inner surface by an enlarged distal tip of an elongate wire that extends within a lumen defined by the inner surface of the sidewall. An operator may move the distal tip of the wire out through a distal opening of the lumen, thereby pushing the free end of the tether out from engagement with the surface, to untether the device from the catheter.

17 Claims, 9 Drawing Sheets

(51) Int. Cl.
*A61N 1/372* (2006.01)
*A61M 25/01* (2006.01)
*A61N 1/375* (2006.01)
*A61B 17/34* (2006.01)

(52) U.S. Cl.
CPC ........... *A61N 1/372* (2013.01); *A61N 1/3756* (2013.01); *A61M 2210/125* (2013.01); *A61N 1/37205* (2013.01)

(58) Field of Classification Search
CPC .................. A61N 1/3756; A61N 1/057; A61N 2001/0578; A61B 17/3468; A61B 6/12; A61B 2017/00243
USPC .................................. 606/129; 607/119, 122
See application file for complete search history.

(56) References Cited

U.S. PATENT DOCUMENTS

| | | |
|---|---|---|
| 7,316,708 B2 | 1/2008 | Gordon et al. |
| 8,615,310 B2 | 12/2013 | Khairkhahan et al. |
| 2007/0073098 A1 | 3/2007 | Lenker et al. |
| 2010/0268204 A1 | 10/2010 | Tieu et al. |
| 2012/0172690 A1 | 7/2012 | Anderson et al. |
| 2012/0172891 A1 | 7/2012 | Lee |
| 2013/0103047 A1 | 4/2013 | Steingisser et al. |
| 2013/0253347 A1 | 9/2013 | Griswold et al. |
| 2013/0281988 A1 | 10/2013 | Magnin et al. |
| 2015/0094668 A1 | 4/2015 | Wood et al. |

OTHER PUBLICATIONS

Tran, et al., "Interventional Medical Systems, Tools, and Subassemblies", U.S. Appl. No. 14/231,976, filed Apr. 1, 2014, 17 pages.

INTERVENTIONAL MEDICAL SYSTEMS AND ASSOCIATED TETHERING ASSEMBLIES AND METHODS

CROSS-REFERENCE TO RELATED APPLICATIONS

This application claims the benefit of U.S. Provisional Application No. 62/132,662, filed on Mar. 13, 2015. The disclosure of the above application is incorporated herein by reference in its entirety.

FIELD OF THE DISCLOSURE

The present disclosure pertains to interventional medical systems, and more particularly to associated tethering assemblies and methods.

BACKGROUND

Figure 1:
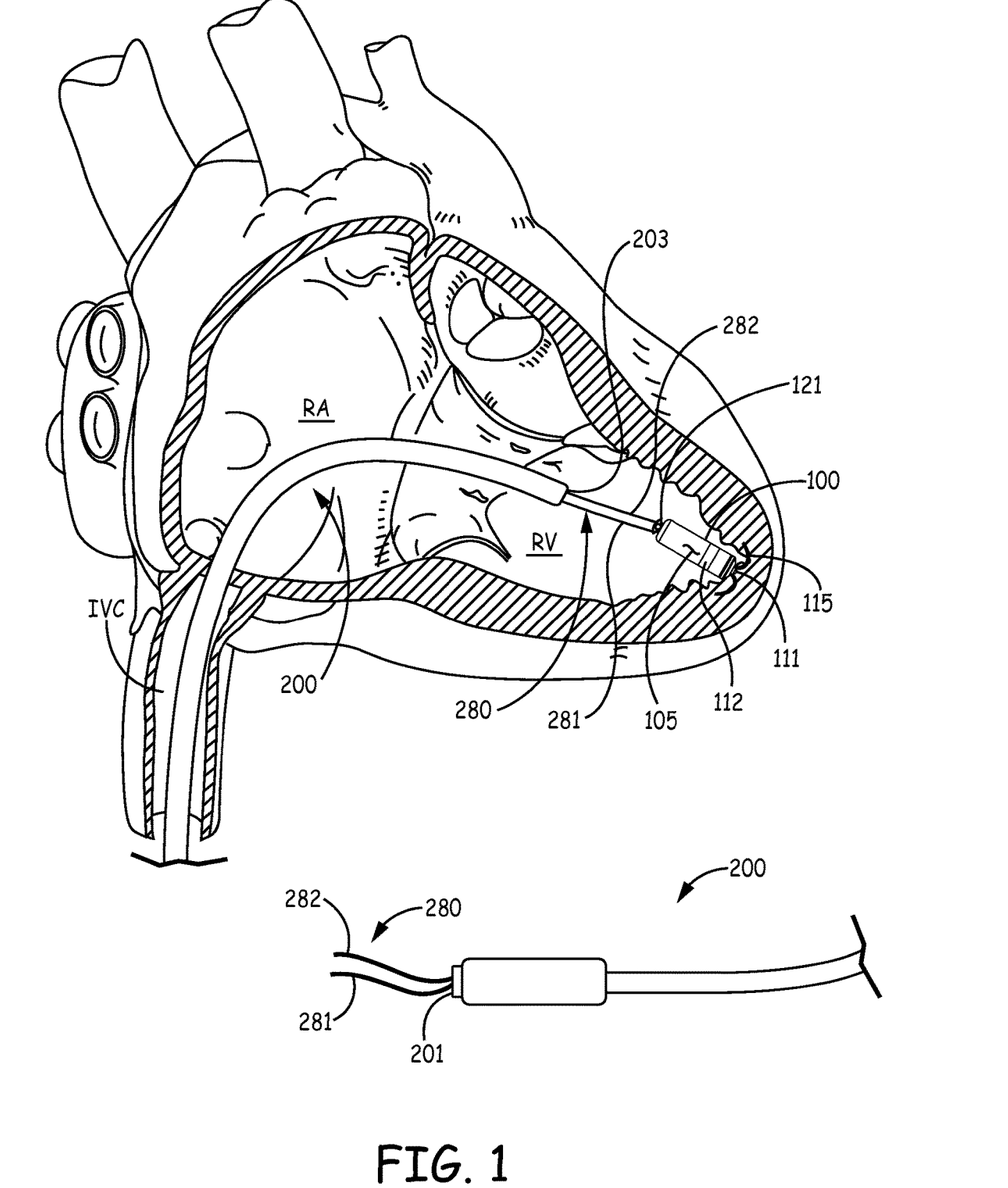
FIG. 1 is a schematic showing an exemplary implant of a relatively compact medical device, via an exemplary delivery catheter.

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, within the right ventricle RV of the heart. With reference to FIG. 1, such a device 100 is illustrated, wherein an hermetically sealed housing 105, preferably formed from a biocompatible and biostable metal such as titanium, contains an electronic controller and associated power source (not shown), to which at least one electrode 111 is coupled, for example, by a hermetic feedthrough assembly (not shown) like those known to those skilled in the. Housing 105 may be overlaid with an insulative layer, for example, medical grade polyurethane, parylene, or silicone, and a portion of the insulation layer may be removed to form another electrode 112, for example, to provide bipolar pacing and sensing in conjunction with electrode 111.

FIG. 1 shows device 100 having been deployed by an operator out from a distal opening 203 of a delivery catheter 200, which the operator has maneuvered up through the inferior vena cava IVC and across the right atrium RA into the right ventricle RV. The deployed device 100 is shown fixed at an implant site by a fixation member 115 thereof, but still secured to catheter 200 by a tether 280 that extends out from distal opening 203 of catheter 200.

Securing device 100 to catheter 200 with tether 280 is typically accomplished by looping tether 280 through an attachment feature 121 of device 100 and threading first and second lengths 281, 282 of tether 280 through one or more lumens of catheter 200 such that opposing ends thereof protrude out from a proximal opening 201 of catheter 200. After deploying device 100, the operator can grasp the ends of lengths 281, 282 and tug on tether 280, for example, to test the fixation of device 100 at the implant site, and/or to apply a greater force to tether 280 to remove device 100 from the implant site for repositioning at a more suitable site, if necessary. If satisfied with the implant of device 100, the operator can untether device 100 from catheter 200 by releasing, for example, the end of tether length 281, and then pulling on the end of the other tether length 282, thereby withdrawing an entirety of length 282 proximally through delivery catheter 200 so that the other length 281 is pulled distally and through device tether attachment feature 121, out from engagement therewith. The above-described procedures associated with tether 280 may be somewhat tedious.

SUMMARY

The present disclosure pertains to improved apparatus and methods related to the tethering of implantable medical devices in the context of deploying the devices at an implant site via a delivery catheter. According to some embodiments, an interventional medical system includes an implantable medical device and a delivery catheter for deploying the device at an implant site, wherein the device is tethered to the catheter by a length of a tether, which extends through an attachment feature of the device, and which includes a secured end and a free end, wherein the secured end is fixedly coupled to a tubular member of the catheter in proximity to a distal end thereof, and the free end is engaged against an inner surface of a relatively rigid sidewall that extends within the tubular member. The free end of the tether may be engaged against the inner surface by an enlarged distal tip of an elongate wire that extends within a lumen defined by the inner surface of the sidewall of the catheter. According to some methods, an operator first inserts the free end of the tether into the lumen, through a distal opening thereof, and then moves the wire proximally within the lumen so that the enlarged distal tip thereof enters into the lumen through the distal opening, thereby engaging and holding the free end of the tether against the inner surface of the sidewall. According to some embodiments, the distal tip of the wire engages and holds the inserted free end of the tether against the inner surface so that the wire can be moved proximally and distally to pull and push, respectively, a portion of the length of the tether within the lumen. To untether the device from the catheter, the operator may move the wire distally within the lumen until the distal tip of the wire exits the lumen through the distal opening, thereby pushing the free end of the tether out from engagement with the inner surface of the sidewall.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figures 2A, 2B:
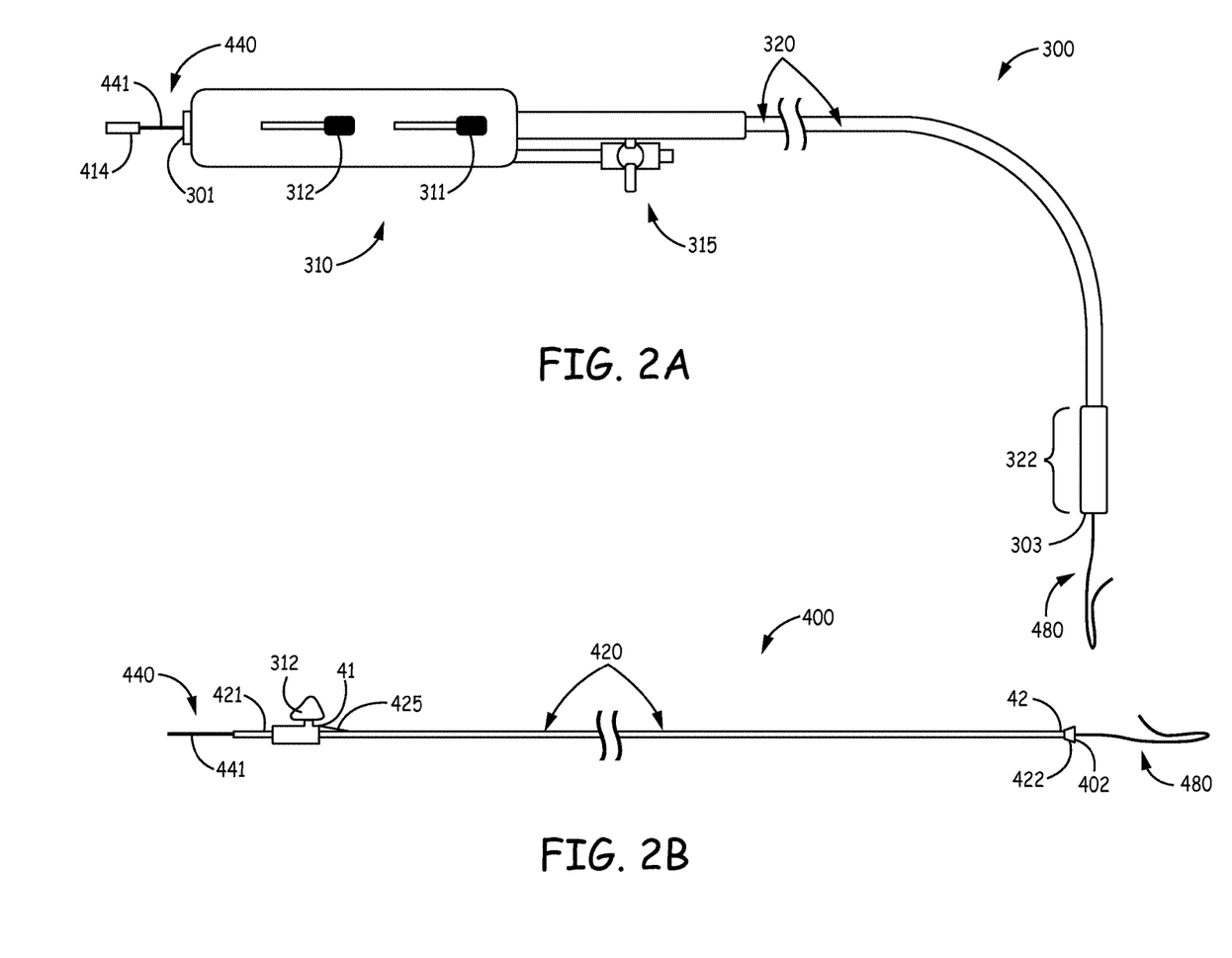
FIG. 2A is a plan view of a delivery catheter, according to some embodiments.
FIG. 2B is a plan view of an inner assembly of the delivery catheter of FIG. 2A, according to some embodiments.

FIG. 2A is a plan view of a delivery catheter 300, which may be employed in an interventional medical system, according to some embodiments. FIG. 2A illustrates catheter 300 including a handle 310, an outer shaft 320, and a flushing assembly 315 coupled to handle 310. FIG. 2A further illustrates a distal-most portion 322 of shaft 320 defining a distal opening 303 thereof, and, as will be described in greater detail below, distal-most portion 322 is sized to contain an implantable medical device for deployment. According to the illustrated embodiment, shaft 320 is slideably engaged around an elongate tubular member 420, which is part of an inner assembly 400 that is shown in the plan view of FIG. 2B, separate from a remainder of catheter 300. Furthermore, shaft 320 is coupled to a control member 311 of handle 310, which is operable to retract and advance shaft 320 relative to tubular member 420, and a lumen of shaft 320 may be in fluid communication with flushing assembly 315. According to some embodiments, outer shaft 320 may be constructed in a similar fashion to a deployment tube of a tool described in co-pending and commonly assigned U.S. patent application Ser. No. 14/039,937.

FIG. 2B illustrates tubular member 420 extending from a proximal end 421 thereof to distal end 422 thereof, wherein distal end 422 defines a distal opening 402 of tubular member 420, and may be configured to generally conform to a proximal end of an implantable medical device (e.g. device 100 of FIG. 1). FIGS. 2A-B further illustrate catheter 300 including a flexible tether 480 and an elongate wire 440, both of which will be described in detail below. Tether 480 is shown protruding out from distal opening 303 of distal-most portion 322, and a proximal end 441 of wire 440 is shown extending proximally from proximal end 421 of tubular member 420 and out through a proximal port opening 301 of handle 310.

Figure 2C:
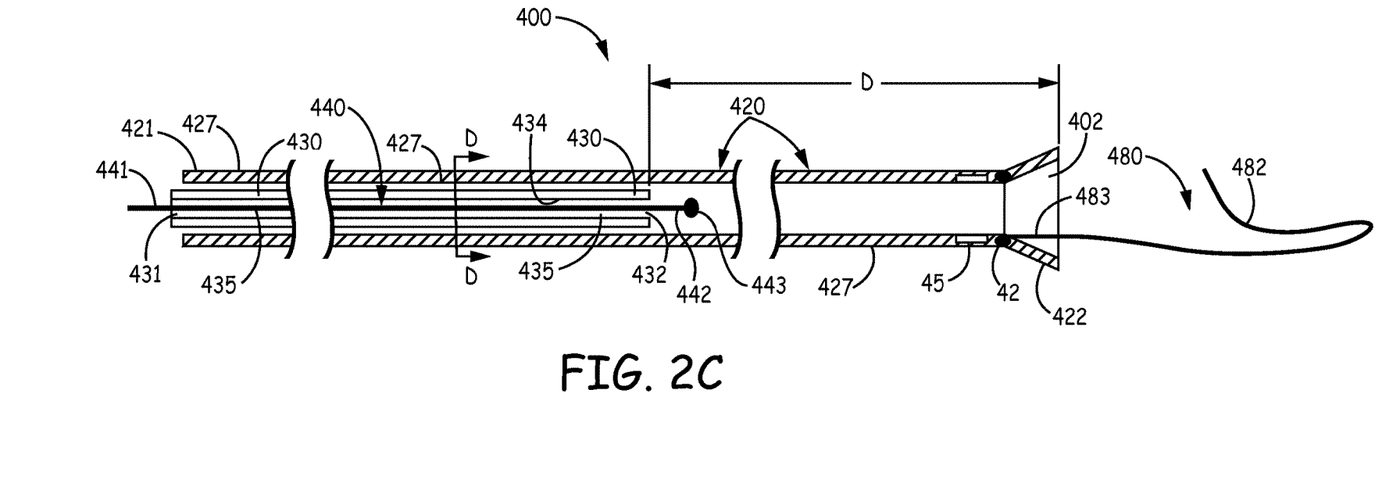
FIG. 2C is a longitudinal cross-section view of the assembly of FIG. 2B, according to some embodiments.

According to some embodiments, assembly 400 may also include a pull wire subassembly. FIG. 2B shows a proximal end 41 of a pull wire 425 extending out from tubular member 420 to be coupled to a second control member 312 of handle 310, wherein a distal end of pull wire 425 is anchored in proximity to distal end 422 of tubular member 420, for example, being coupled to an anchor band 45 (FIG. 2C). According to the illustrated embodiment, movement of second control member 312, actuates pull wire 425 to bend tubular member 420 and shaft 320, for example, to facilitate maneuvering delivery catheter 300 to an implant site.

With further reference to FIG. 2B, in conjunction with the longitudinal cross-section view of FIG. 2C, tether 480 is part of inner assembly 400 being attached to tubular member 420. FIG. 2C shows tether 480 extending over a length between a free end 482 thereof and a secured end 483 thereof, which is fixedly coupled to tubular member 420 in proximity to distal end 422. The length of tether 480, for example, formed from a polyester fiber having a fluoropolymer coating such as PTFE, has a cross-section sized for threading through an aperture of an attachment feature of an implantable medical device, for example, an aperture 109 of feature 121 of device 100, which is shown FIG. 3A. According to some embodiments, distal end 422 of tubular member 420 is a cone member that is coupled to a remainder of tubular member 420 by a thermally bonded junction 42, wherein secured end 483 of tether 480 is fused to tubular member 420 at junction 42, for example, while forming junction 42. In these embodiments, the cone member may be formed from a polyether block amide, for example, PEBAX® 7233, and the remainder of tubular member 420 may be formed by a dual lumen tube 427, for example, as illustrated in the cross-section view of FIG. 2D; tube 427 may be extruded polyether block amide, polyurethane, or silicone rubber, or a composite thereof, and may include an overlay (not shown), for example, formed of braid-reinforced polyether block amide.

Figure 2D:
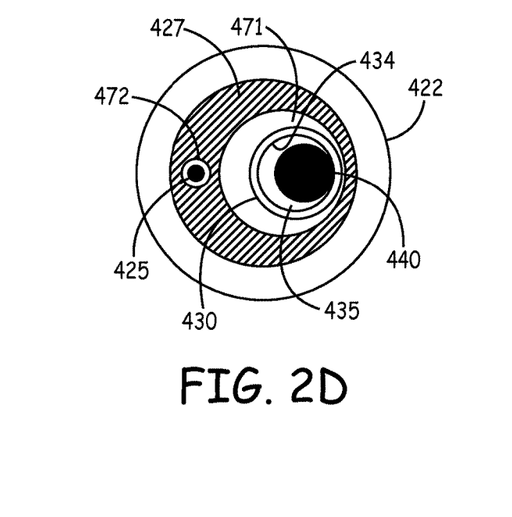
FIG. 2D is an axial cross-section view through section line D-D of FIG. 2C, according to some embodiments.

FIGS. 2C-D further illustrate wire 440 extending within an elongate lumen 435 of assembly 400, which is defined by an inner surface 434 of a relatively rigid sidewall 430 that extends within tubular member 420, for example, within a lumen 471 of tube 427, which extends alongside another lumen 472 in which pull wire 425 extends. Lumen 435 is shown extending from a proximal opening 431 thereof to a distal opening 432 thereof, wherein proximal opening 431 is located in proximity to proximal end 421 of tubular member 420, being in fluid communication with proximal port opening 301 of handle 310 (FIG. 2A), and distal opening 432, being in fluid communication with distal opening 402 of tubular member 420, is proximally offset therefrom by a distance D. According to an exemplary embodiment, distance D is approximately 20 centimeters, and sidewall 430 may be a medical grade stainless steel hypo-tube, for example, having an inner diameter of approximately 0.019 inch (0.48 mm) and an outer diameter of approximately 0.026 inch (0.66 mm), wherein a proximal end of the hypo-tube extends proximally from proximal end 421 of tubular member 420 to be secured within handle 310, for example, by an adhesive bond.

With further reference to FIG. 2C, wire 440 includes a distal portion 442 and an enlarged distal tip 443 that terminates distal portion 442, wherein a length of wire 440 from proximal end 441 to distal tip 443 is greater than a length of sidewall 430. According to the illustrated embodiment, wire 440 is moveable within lumen 435 between a first position and a second position, wherein distal tip 443 is located distal to distal opening 432 of lumen 435 when wire 440 is in the first position (FIG. 2C), and distal tip 443 is located within lumen 435, recessed proximally from distal opening 432, when wire 440 is in the second position, for example, as shown in FIG. 3D. Furthermore, enlarged distal tip 443 has a size and configuration to engage and hold free end 482 of tether 480 against inner surface 434 of sidewall 430, when free end 482 is inserted into lumen 435 and distal tip 443 is retracted into lumen 435, both through distal opening 432. Thus, tether 480 may be employed to tether an implantable medical device to catheter 300 in an interventional medical system, as described below in conjunction with FIGS. 3A-D, according to some embodiments and methods.

Figure 3A:
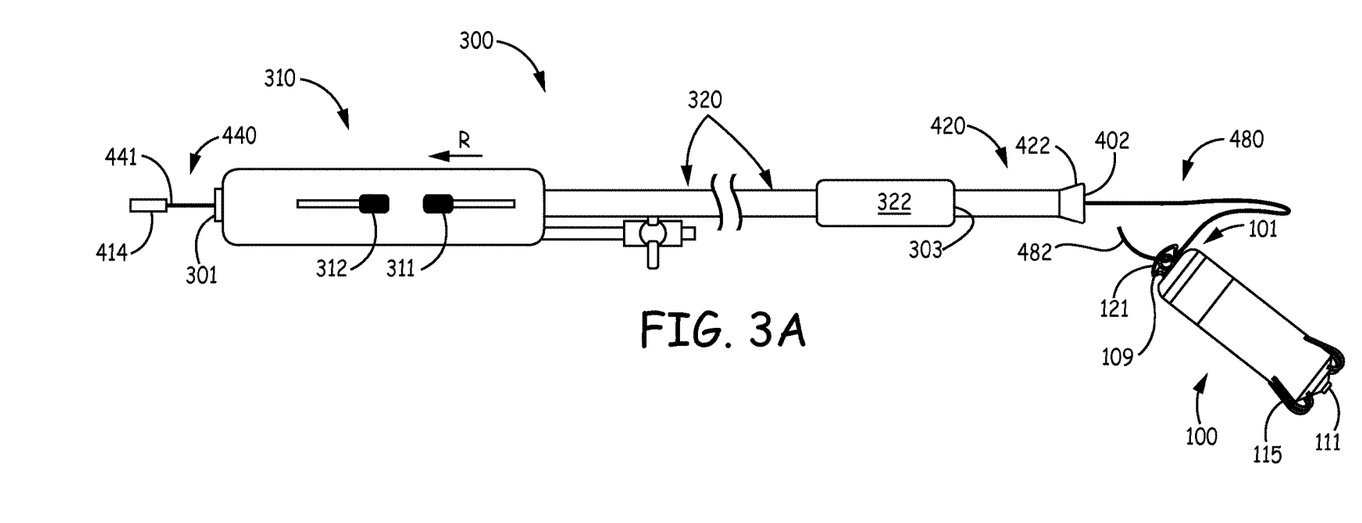
FIGS. 3A-D are schematics outlining some methods of the present invention.
Figure 3B:
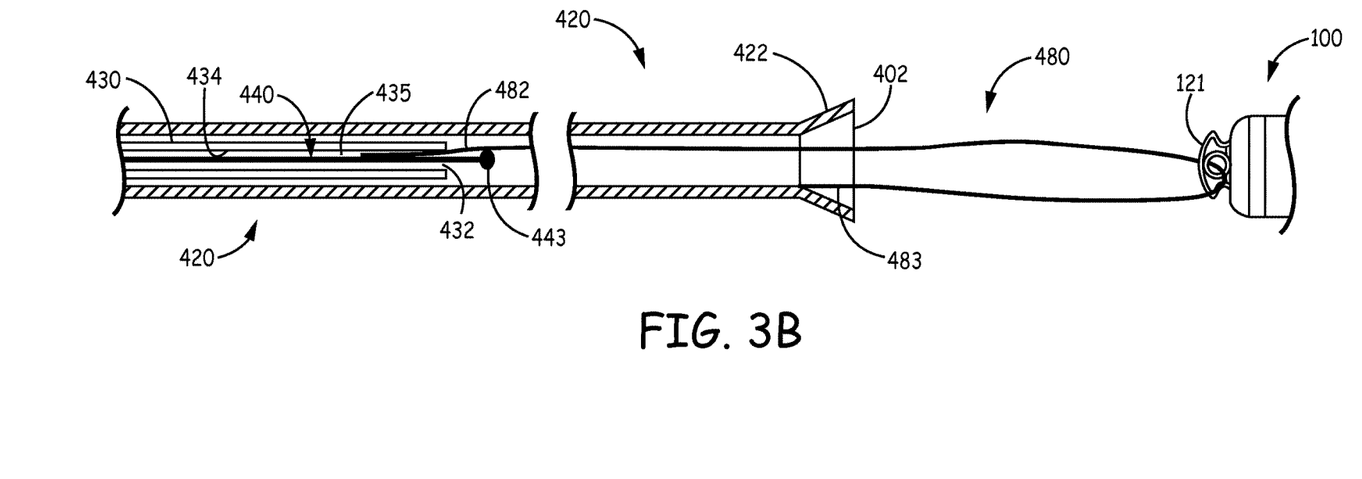
Figure 3C:
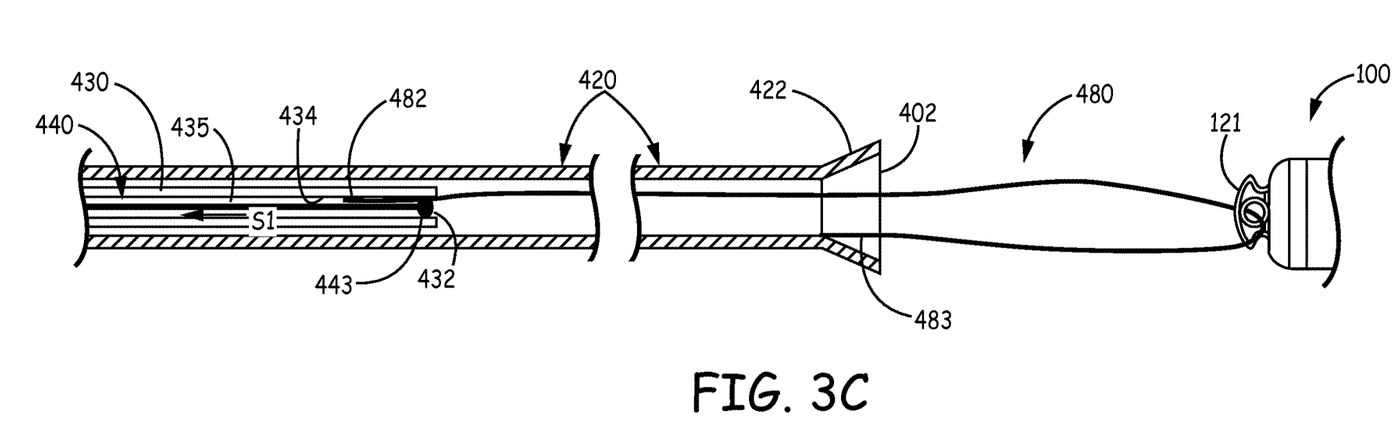
Figure 3D:
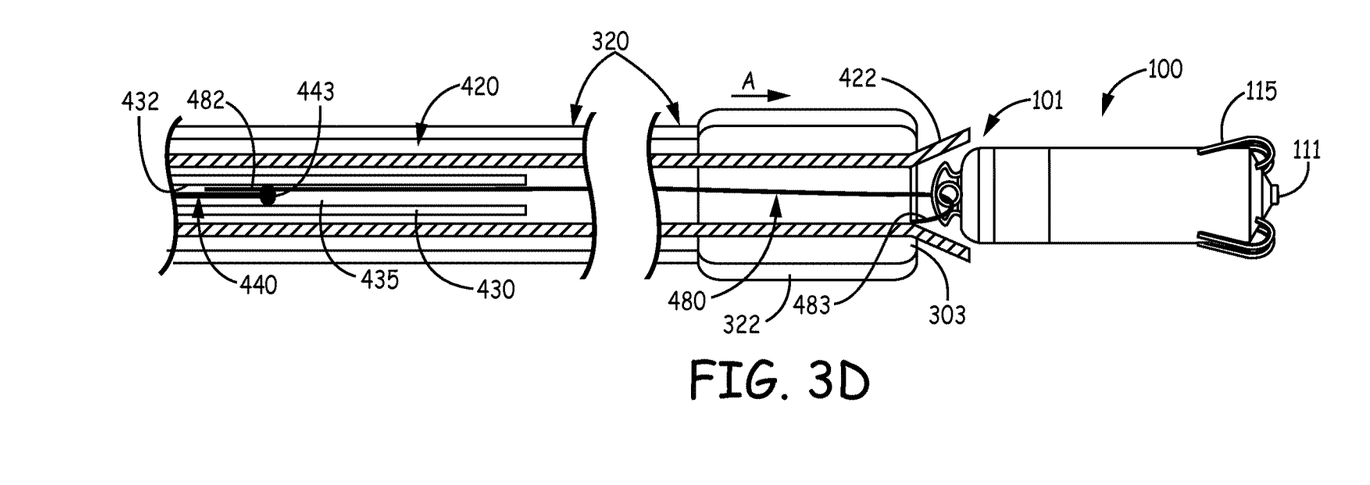

FIGS. 3A-D are schematics outlining some methods for tethering implantable medical device 100 to delivery catheter 300. FIG. 3A illustrates outer shaft 320 retracted relative to tubular member 420, for example, by moving control member 311 proximally per arrow R, so that distal end 422 is exposed, and illustrates free end 482 of tether 480 having been threaded through aperture 109 of device attachment feature 121. FIG. 3B illustrates tether free end 482 having been inserted into lumen 435, through distal opening 432, while wire 440 is in the first position, at which enlarged distal tip 443 is located distal to distal opening 432. FIG. 3C illustrates wire 440 having been moved proximally within lumen 435 so that distal tip 443 enters into lumen 435 through distal opening 432, thereby engaging and holding the inserted free end 482 of tether 480 against inner surface 434 of sidewall 430. Thus, once the operator has retracted distal tip 443 into lumen 435, the operator can continue to move wire 440 proximally within lumen 435, per arrow S1, to pull the engaged free end 482 of tether 480 proximally along inner surface 434, thereby bringing the threaded length of tether 480 into lumen 435 until a proximal end 101 of device 100 contacts distal end 422 of tubular member 420, for example, as illustrated in FIG. 3D. FIG. 3D illustrates wire 440 having been moved proximally, into the above described second position. With further reference to FIG. 3A, proximal end 441 of wire 440 may be terminated by an enlarged grip member 414 that provides the operator with an ergonomic interface for moving wire 440 within lumen 435.

Figure 4A:
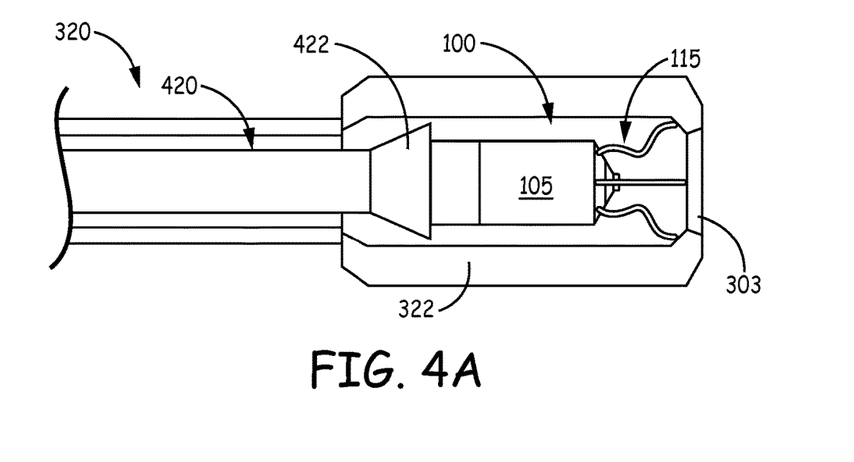
FIGS. 4A-D are schematics outlining some additional methods.

FIG. 3D further illustrates outer shaft 320 being advanced distally, per arrow A, relative to tubular member 420 and device 100, to move shaft 320 over device 100 so that distal-most portion 322 contains device 100, for example, as illustrated in FIG. 4A. With further reference to FIG. 4A, advancing outer shaft 320 over device 100 moves a plurality of fixation fingers of fixation member 115 from a relaxed condition (FIG. 3D) to an extended condition. Fixation member 115 may be cut from Nitinol tubing, according to methods known in the art, and fixation member 115 may be mounted to device housing 105 in a manner similar to that described for a fixation component 102 in co-pending and commonly assigned United States Patent Application 2012/0172690. The super-elastic nature of Nitinol allows the fingers thereof to elastically deform between the relaxed and extended conditions. According to some methods, prior to advancing outer shaft 320 per arrow A, the operator may secure a proximal section of wire 440, just distal to grip member 441, to a proximal end of catheter 300, for example, in proximity to proximal port opening 301 of handle 310 (FIGS. 2A and 3A). According to some embodiments, proximal port opening 301 is defined by a valve member, for example, a Tuohy Borst type known to those skilled in the art, which the operator may open and close around the proximal section of wire 440.

Figure 4B:
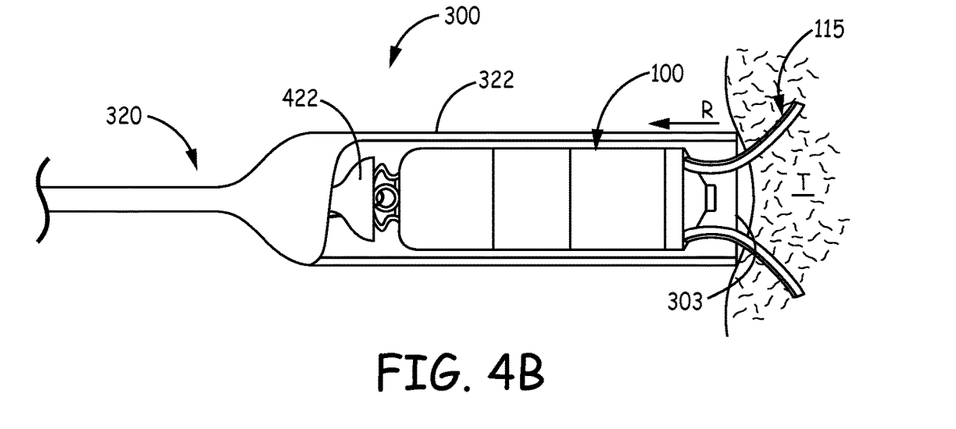
Figure 4C:
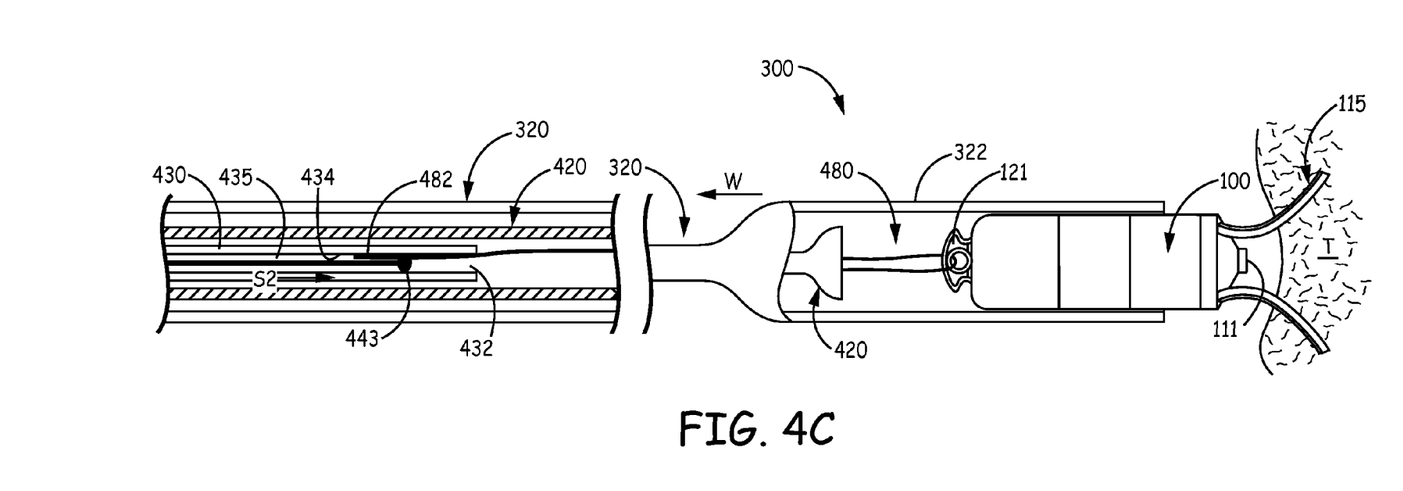
Figure 4D:
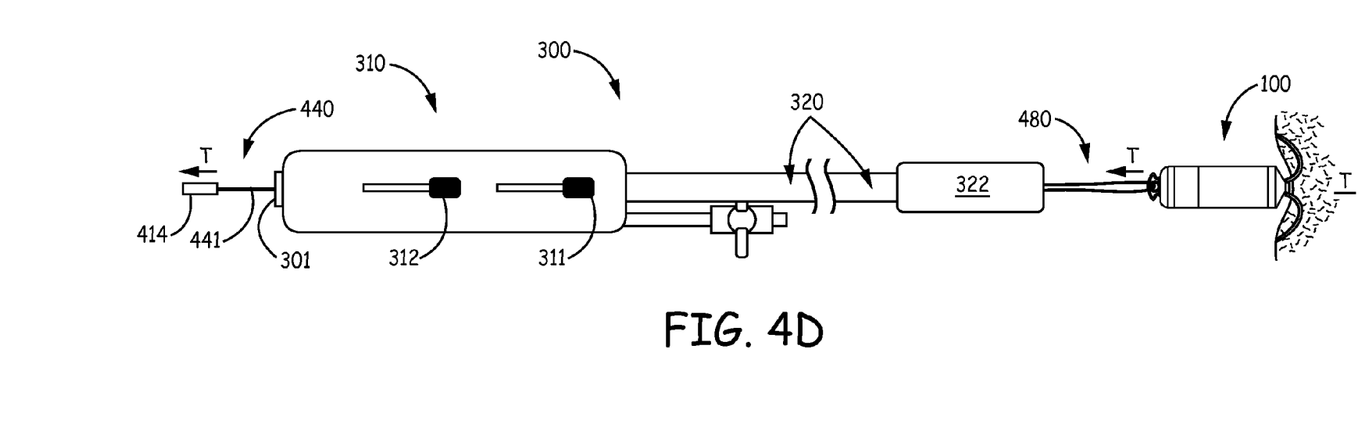

FIGS. 4A-D are schematics outlining some methods for deploying device 100 with catheter 300, and untethering device 100 therefrom. The extended condition of the fixation fingers, as shown in FIG. 4A, allows for initial engagement thereof with tissue, after the operator has maneuvered catheter 300 into proximity with an implant site and when the operator retracts outer shaft 320, per arrow R, for example, as shown in FIG. 4B. With reference back to FIG. 1, catheter 300, like catheter 200, can be maneuvered up through the inferior vena cava IVC and into the right ventricle RV, from the right atrium RA, to approach the implant site. FIG. 4B shows fingers of device fixation member 150 initially engaging tissue T at the implant site as outer tubular member 320 of catheter is retracted per arrow R. When fixation member 150 of device 100 is fully engaged with tissue T, as seen in FIG. 4C, delivery catheter 300 can be withdrawn relative to device 100, per arrow W, but only after the operator has created some slack in tether 480. FIG. 4C illustrates wire 440 moved distally, per arrow S2, to push a portion of the length of tether 480 out from lumen 435 through distal opening 432. If the operator desires to keep device tethered to catheter 300, for example, while evaluating the performance of electrode 111 at the implant site, the operator will keep enlarged distal tip 443 of wire 440 within lumen 435 to hold tether free end 482 against inner surface 434 of sidewall 430. Thus, the operator can move catheter 300 away from the implant site, as illustrated in FIG. 4D, while the implanted device 100 is being evaluated. The operator can also evaluate fixation of device 100 by pulling on wire 440 to apply a tug force, per arrow T, to device 100 through tether 480. Otherwise, to untether the implanted device 100 from catheter 300, the operator may move wire 440 back into the first position (FIG. 3B), to push free end 482 of tether 480 out from engagement with inner surface 434 of sidewall 430, and then withdraw catheter 300 further, to pull tether free end 482 through aperture 109 of device attachment feature 121.

Figure 5:
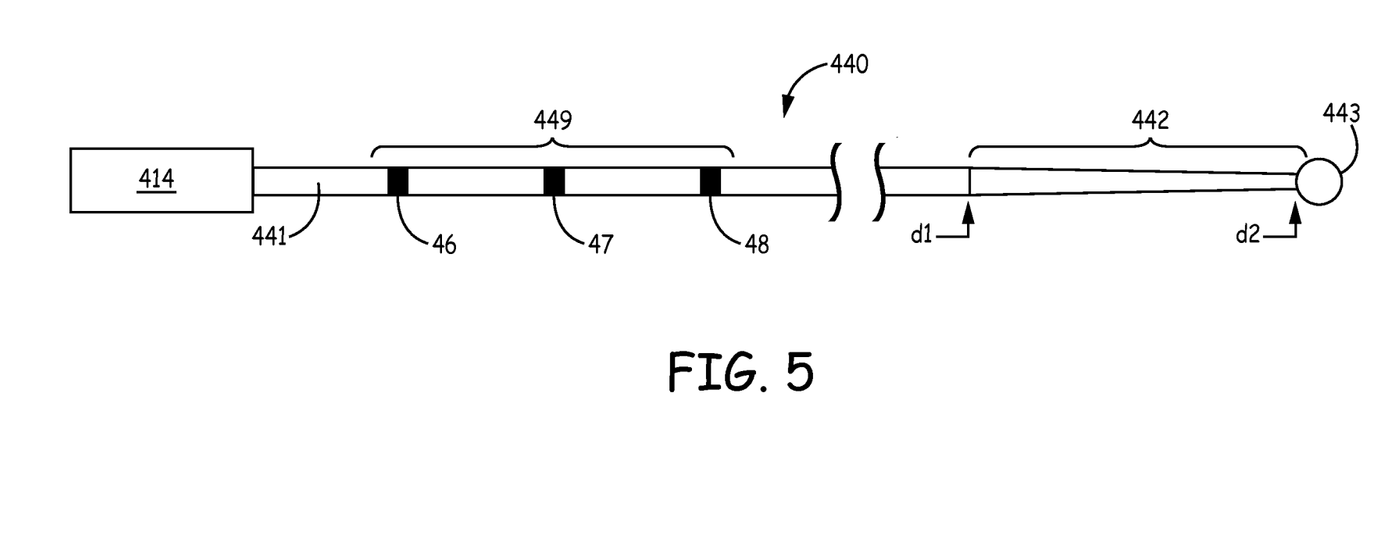
FIG. 5 is a plan view of an elongate wire of the assembly of FIG. 2B, according to some embodiments.

FIG. 5 is an enlarged plan view of elongate wire 440, according to some embodiments. FIG. 5 illustrates distal portion 442 of wire 440 tapering from a first diameter d1 to a second diameter d2, which is located adjacent to enlarged distal tip 443 and is smaller than both a cross-section of distal tip 443 and first diameter d1. According to an exemplary embodiment, wire 440 is formed according to methods known to those skilled in the art, from medical grade stainless steel rod stock, to which grip 414, for example, being an injection molded medical grade plastic part, is secured; and a diameter of the length of wire 440 that extends between proximal end 441 and distal portion 442, may be approximately equal to first diameter d1, for example, between approximately 0.015 in (0.38 mm) and approximately 0.017 in (0.43 mm). FIG. 5 further illustrates wire 440 including an optional marker zone 449, which is located in proximity to proximal end 441 of wire 440, wherein marker zone 449 includes at least a first, proximal mark 46, and a second, distal mark 48, and may further include an intermediate mark 47. Marker zone 449 provides the operator with an indication of the location of distal tip 443 of wire 440 relative to distal opening 432 of lumen 435, when wire 440 extends therein, for example, as described in conjunction with FIGS. 6A-C.

Figure 6A:
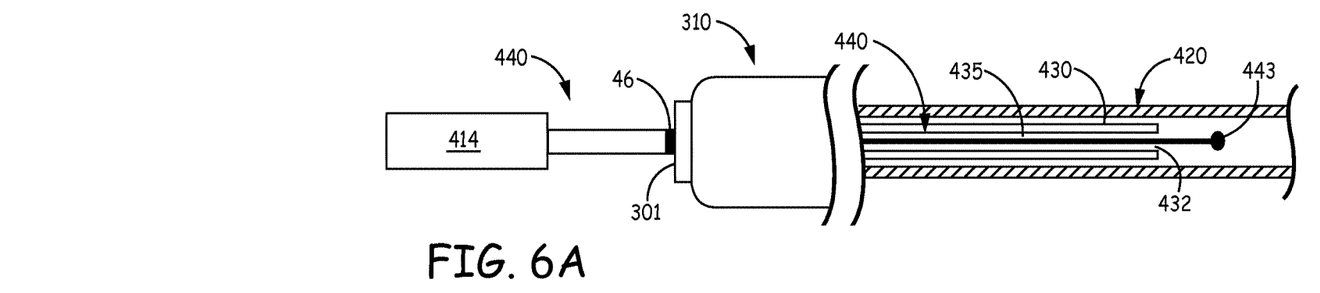
FIGS. 6A-C are schematics demonstrating employment of an optional marker zone of the wire shown in FIG. 5, according to some methods.
Figure 6B:
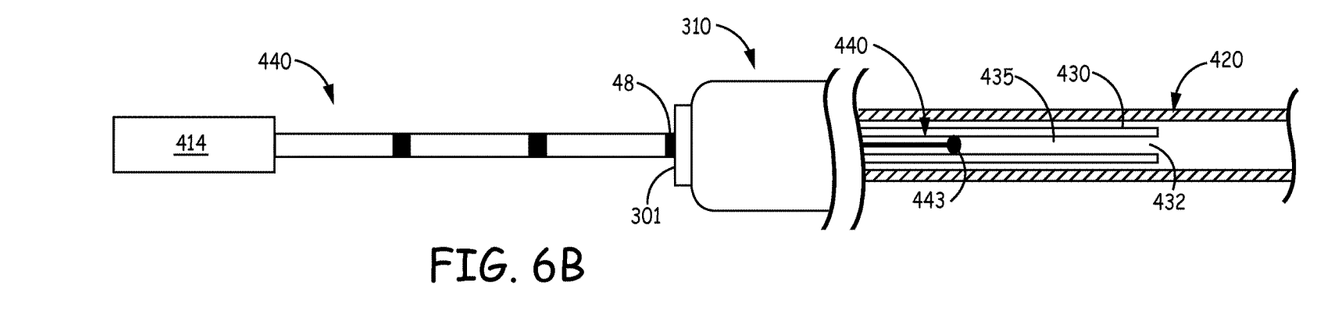
Figure 6C:
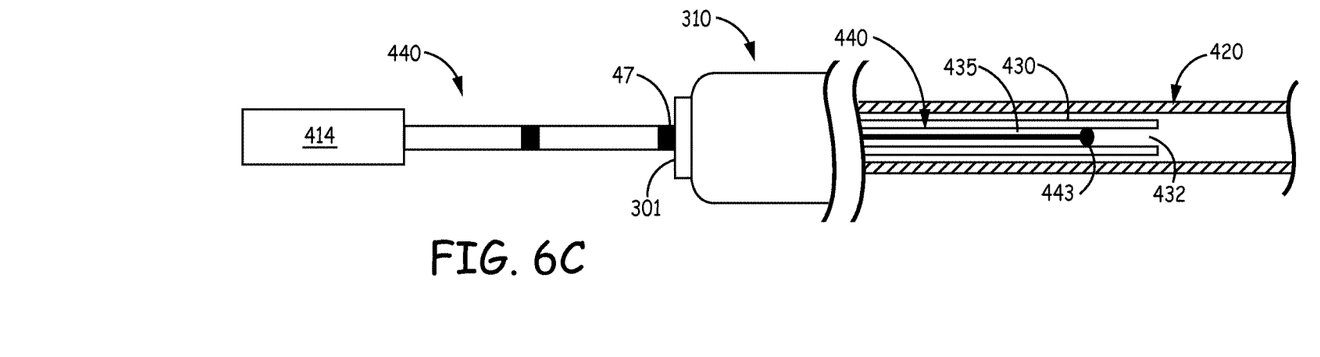

FIGS. 6A-C are schematics demonstrating the employment of marker zone 449, according to some methods. FIG. 6A illustrates first mark 46 being approximately aligned with proximal port opening 301 of catheter handle 310 to indicate to the operator that wire 440 is in the first position at which distal tip 443 is located distal to distal opening 432 of lumen 435. FIG. 6B illustrates second mark 48 being approximately aligned with proximal port opening 301 to indicate to the operator that wire 440 is in the second position, at which distal tip 443 is within lumen 435 and recessed proximally from distal opening 432, and wherein the second position is also that at which a sufficient length of tether 480 has been brought into lumen 435 so that proximal end 101 of the device 100 contacts the distal end of the tubular member, as illustrated in FIG. 3D. FIG. 6C illustrates intermediate mark 47 approximately aligned with proximal port opening 301 when wire 440 is in an intermediate position, which also corresponds to wire distal tip 443 being located within lumen 435, but in closer proximity to distal opening 432 than when wire 440 is in the second position. Intermediate mark 47 may be useful to help the operator create some slack in tether 480, for example, as illustrated in FIG. 4C, without inadvertently releasing tether free end 482 from engagement with inner surface 434 of sidewall 430.

In the foregoing detailed description, the invention has been described with reference to specific embodiments. However, it may be appreciated that various modifications and changes can be made without departing from the scope of the invention as set forth in the appended claims.

The invention claimed is:

1. An interventional medical system comprising an implantable medical device and a delivery catheter for deploying the device at an implant site, and the catheter comprising:
   an elongate tubular member extending from a proximal end thereof to a distal end thereof, the distal end defining a distal opening of the tubular member;
   a relatively rigid sidewall extending within the tubular member and having an inner surface defining a lumen, the lumen extending over a length of the sidewall from a proximal opening thereof to a distal opening thereof, the distal opening of the lumen being in fluid communication with the distal opening of the tubular member;
   an elongate wire including a proximal end, a distal portion, and an enlarged distal tip that terminates the distal portion, a length of the wire, from the proximal end thereof to the distal tip thereof being greater than the length of the sidewall, and the wire extending within the elongate lumen defined by the inner surface of the sidewall and being moveable therein between a first position and a second position, the distal tip being located distal to the distal opening of the lumen in the first position, and the distal tip being located within the lumen and recessed proximally from the distal opening of the lumen in the second position;
   a flexible tether extending over a length between a free end thereof and a secured end thereof, the secured end being fixedly coupled to the tubular member in proximity to the distal end thereof, and the length of the tether having a cross-section sized for threading through an aperture of an attachment feature of the device; and
   a handle secured to the sidewall and the proximal end of the tubular member such that the sidewall and the tubular member are fixed in relation to one another and extend distally from the handle, the handle including a proximal port opening in fluid communication with the proximal opening of the lumen defined by the inner surface of the sidewall, the proximal end of the wire extending proximally out from the proximal port opening to be accessible for moving the wire between the first and second positions; and
   wherein the enlarged distal tip of the wire has a size and configuration to engage and hold the free end of the tether against the inner surface of the sidewall, when the free end of the tether is inserted into the lumen defined by the inner surface, and when the tip of the wire is retracted into the lumen from the first position; and
   when the enlarged distal tip of the wire engages and holds the free end of the tether against the inner surface of the sidewall, and the wire is moved to the second position, the free end of the tether is pulled by the tip proximally along the inner surface to bring a portion of the length of the tether into the lumen so that a proximal end of the device contacts the distal end of the tubular member.

2. The system of claim 1, wherein the distal opening of the lumen defined by the inner surface of the sidewall of the catheter is offset proximally from the distal opening of the tubular member of the catheter by a distance of approximately 20 centimeters.

3. The system of claim 1, wherein the distal end of the tubular member of the catheter is enlarged from a remainder of the tubular member, being configured to generally conform to the proximal end of the device.

4. The system of claim 3, wherein the distal end of the tubular member comprises a cone member coupled to a remainder of the tubular member by a thermally bonded junction, the secured end of the tether of the catheter being fused to the tubular member at the thermally bonded junction.

5. The system of claim 3, wherein the catheter further comprises an outer shaft slideably engaged around the tubular member, the outer shaft including a distal-most portion sized to contain the device and the distal end of the tubular member therein, when the device is in contact therewith.

6. The system of claim 1, wherein:
   the catheter further comprises a pull wire subassembly including an elongate pull wire and an anchor band, the pull wire extending from a proximal end thereof to a distal end thereof, and the anchor band being mounted to the tubular member, in proximity to the distal end thereof, and coupled to the distal end of the pull wire; and
   the tubular member of the catheter comprises a dual lumen tube having a first lumen in which the sidewall extends and a second lumen in which the pull wire extends; and
   the handle further includes a control member coupled to the proximal end of the pull wire.

7. The system of claim 1, wherein the proximal port opening of the handle of the catheter is defined by a valve member being operable to secure the wire of the catheter therein, thereby preventing the moving of the wire.

8. The system of claim 1, wherein the elongate wire of the catheter further includes a marker zone located in proximity to the proximal end thereof, the marker zone comprising a first mark and a second mark, the first mark being approximately aligned with the proximal port opening of the handle when the wire is in the first position, and the second mark being approximately aligned with the proximal port opening when the wire is in the second position.

9. The system of claim 8, wherein the marker zone of the wire further comprises an intermediate mark located in between the first mark and the second mark, the intermediate mark being approximately aligned with the proximal port opening of the handle when the wire is in an intermediate position, the intermediate position corresponding to the enlarged distal tip of the wire being located within the lumen formed by the inner surface of the sidewall of the tubular member and in closer proximity to the distal opening of the lumen than when the wire is in the second position.

10. The system of claim 1, wherein the distal portion of the elongate wire of the catheter tapers from a first diameter to a second diameter, the second diameter being adjacent the enlarged distal tip of the wire and being smaller than a cross-section of the distal tip and smaller than the first diameter.

11. The system of claim 1, wherein the implantable medical device comprises an electronic controller and an associated power source, a hermetically sealed housing containing the controller and power source, an electrode electrically coupled to the controller and mounted to the housing, and a fixation member mounted to a distal end of the housing; and the attachment feature of the device is mounted to the proximal end of the housing.

12. An assembly for a delivery catheter, the catheter for deploying an implantable medical device at an implant site, and the assembly comprising:
   an elongate tubular member extending from a proximal end thereof to a distal end thereof, the distal end defining a distal opening of the tubular member;
   a relatively rigid sidewall extending within the tubular member and having an inner surface defining an elongate lumen, the lumen extending over a length of the sidewall from a proximal opening thereof to a distal opening thereof, the distal opening of the lumen being in fluid communication with the distal opening of the tubular member;
   an elongate wire including a proximal end, a distal portion, and an enlarged distal tip that terminates the distal portion, a length of the wire, from the proximal end thereof to the distal tip thereof being greater than the length of the sidewall, and the wire extending within the elongate lumen defined by the inner surface of the sidewall and being moveable therein between a first position and a second position, the distal tip being located distal to the distal opening of the lumen in the first position, and the distal tip being located within the lumen and recessed proximally from the distal opening of the lumen in the second position; and
   a flexible tether extending over a length between a free end thereof and a secured end thereof, the secured end being fixedly coupled to the tubular member in proximity to the distal end thereof, and the length of the tether having a cross-section sized for threading through an aperture of an attachment feature of the device;
   wherein the enlarged distal tip of the wire has a size and configuration to engage and hold the free end of the tether against the inner surface of the sidewall, when the free end of the tether is inserted into the lumen defined by the inner surface, and when the tip of the wire is retracted into the lumen from the first position; and
   when the enlarged distal tip of the wire engages and holds the free end of the tether against the inner surface of the sidewall, and the wire is moved to the second position, the free end of the tether is pulled by the tip proximally along the inner surface to bring a portion of the length of the tether into the lumen.

13. The assembly of claim 12, wherein the distal opening of the lumen defined by the inner surface of the sidewall is offset proximally from the distal opening of the tubular member by a distance of approximately 20 centimeters.

14. The assembly of claim 12, wherein the distal end of the tubular member is enlarged from a remainder of the tubular member, being configured to generally conform to a proximal end of the device.

15. The assembly of claim 14, wherein the distal end of the tubular member comprises a cone member coupled to a remainder of the tubular member by a thermally bonded junction, the secured end of the tether being fused to the tubular member at the thermally bonded junction.

16. The assembly of claim 12, further comprising:
   a pull wire subassembly, the subassembly including an elongate pull wire and an anchor band, the pull wire extending from a proximal end thereof to a distal end thereof, and the anchor band being mounted to the tubular member, in proximity to the distal end thereof, and coupled to the distal end of the pull wire; and
   wherein the tubular member comprises a dual lumen tube having a first lumen in which the sidewall extends and a second lumen in which the pull wire extends.

17. The assembly of claim 12, wherein the distal portion of the elongate wire tapers from a first diameter to a second diameter, the second diameter being adjacent the enlarged distal tip of the wire and being smaller than a cross-section of the distal tip and smaller than the first diameter.

* * * * *